United States Patent [19]

Rust et al.

[11] Patent Number: 5,605,794

[45] Date of Patent: Feb. 25, 1997

[54] METHOD OF DETECTING VARIANT NUCLEIC ACIDS

[75] Inventors: Stephan Rust; Harald Funke; Gerd Assmann, all of Munster; Christoph Kessler, Dorfen; Rudiger Rueger, Seeshaupt, all of Germany

[73] Assignee: Boehringer Mannheim GmbH, Mannheim, Germany

[21] Appl. No.: 205,777

[22] Filed: Mar. 3, 1994

Related U.S. Application Data

[63] Continuation of Ser. No. 939,479, Sep. 4, 1992, abandoned.

[30] Foreign Application Priority Data

Sep. 6, 1991 [DE] Germany ............................ 41 29 653.2

[51] Int. Cl.$^6$ .............................. C12Q 1/68; C12P 19/34
[52] U.S. Cl. .................... 435/6; 435/91.1; 435/91.2
[58] Field of Search ............................... 435/5, 6, 91.2, 435/91.1; 536/23.1, 24.3; 935/78

[56] References Cited

FOREIGN PATENT DOCUMENTS

| | | |
|---|---|---|
| 0200362 | 12/1986 | European Pat. Off. . |
| 0201184 | 12/1986 | European Pat. Off. . |
| 0310229 | 4/1989 | European Pat. Off. . |
| 0320308 | 6/1989 | European Pat. Off. . |
| 0329822 | 8/1989 | European Pat. Off. . |
| 0333465 | 9/1989 | European Pat. Off. . |
| 0332435 | 9/1989 | European Pat. Off. . |
| 0373960 | 6/1990 | European Pat. Off. . |
| 0422762 | 4/1991 | European Pat. Off. . |
| WO89/09835 | 10/1989 | WIPO . |
| 8910414 | 11/1989 | WIPO . |
| WO90/01069 | 2/1990 | WIPO . |
| 9011372 | 10/1990 | WIPO . |

OTHER PUBLICATIONS

Newton et al Nucleic Acids Research 17,7,2503–2516 (1989) Analysis of any point mutation. The amplification refractory mutation system (ARMS).
Oncogene Research 1,235–241 (1989).
Nucl. Acids Res. 17, 8093–8099 (1989).
Nucl. Acids Res. 18, 999–1005 (1990).
Biochem. Biophys. Res. Commun. 160, 441–447 (1989).
Proc. Nat. Acad. Sci. USA 82, 1585–1588 (1985).
New England Journal of Medicine 317, 985 (1987).
Nucl. Acids Res. 17, 2437–2448 (1989).
Proc. Natl. Acad. Sci. USA 88, 189–193 (1991).
Nucl. Acids Res. 16, 11141–11151 (1988).

*Primary Examiner*—Kenneth R. Horlick
*Attorney, Agent, or Firm*—Nikaido, Marmelstein, Murray & Oram LLP

[57] ABSTRACT

Method of detecting nucleic acids whose nucleotide sequences differ from one another at a position X. The method uses a set of oligonucleotides where the nucleotides found at position X are complementary to a variant nucleic acids only at this position X. However, with respect to the position of another mismatch Y, the nucleotide sequences thereof differ from one another. The invention further addresses reagents for performing the methods as well as reagents and applications of the method.

22 Claims, 11 Drawing Sheets

METHOD OF DETECTING VARIANT NUCLEIC ACIDS

This application is a continuation of application Ser. No. 07/939,479 filed Sep. 4, 1992, abandoned.

The present invention comprises a method for detecting variant nucleic acids, a set of oligonucleotides suitable for this purpose, a reagent kit for performing the method of the invention and various uses and applications of the method in the diagnosis of genes and infections.

Today, the testing of samples for the presence of certain nucleic acids nucleic acid groups gains increasingly more importance. This is partly due to the fact that the nucleotide sequences of a nucleic acid are a feature of each organism. Current attempts in this field focus on the use of only one single difference in the sequence of nucleotides in order to discriminate between nucleic acids. Such differences may be a consequence of nucleotide exchanges caused by point mutation, for example. Natural examples of such closely related nucleic acids are, for example, alleles, i.e. alternative variants of sequences of a given gene on a defined site on a chromosome.

From *Oncogene Research* 1 (1989), 235–241 and *Nucl. Acids Res.* 17 (1989), 8093–8099 a method is known where the area which presumably contains the allelic variant is first amplified in a polymerase chain reaction (PCR) using specially designed primers and is then treated with a restriction enzyme. The alleles can then be diagnosed once they have been analyzed with restriction fragment length polymorphisms (RFLP). Electrophoretic separation of the cleavage products according to size then reveals whether the corresponding allele was or was not contained in the probe. The disadvantage of this procedure is that it requires specific restricitve digestion. Apart from the fact that this is a cumbersome procedure, for each mutation that does not already produce an RFLP, it is necessary that a design for a primer adjacent to the point mutation be possible which should allow digestion with a restriction enzyme that cleaves exactly at the given site. This may be difficult due to the reasons listed in said publications.

EP-A-0 332 435 describes a method for selectively detecting a nucleic acid which differs from an adjacent nucleic acid by only one nucleotide. The effect employed here is the following one: from the oligonucleotides which are hybridized to the nucleic acid to be detected only those can be theoretically extended by means of enzymes where the one nucleotide, which is terminal in direction of extension, is complementary to the corresponding nucleotide of the nucleic acid (of the one allele) to be detected. The oligonucleotide is hence selected such that it is only complementary to the nucleic acid to be tested. Thus, the oligonucleotide hybridized to the other allele is theoretically not extended. It turned out, however, that in practice the oligonucleotide hybridized to the other allele is, though only to a minor extent, also extended. This reduces the sensitivity and, particularly, the specificity of the method. Non-specific extension may easily occur especially when T is part of the 3'-terminal mismatch or when the mismatch is a C:A mismatch (Kwok et al. (1990). *Nucleic Acids Research*, 18:999–1005). In order to increase specificity, EP-A-0 332 435 proposes to select the nucleotide sequence of an oligonucleotide such that the terminal area contains another nucleotide that is not complementary to the corresponding nucleotide of the two nucleic acids. For the detection of both alleles two reactions must be carried out with only one of two alleles being detected per reaction. This procedure requires the synthesis of two allele-specific primers and one complementary strand primer. The sample is amplified in two reactions: once in a PCR with the primer of the complementary strand and one of the allele-specific primers, and in the second parallel reaction, a PCR, it is amplified with the complementary strand primer and the second allele-specific primer. If the suspected allele-specific PCR product is not detected in one of the reactions, it is assumed that the respective allele is not present in the sample. Since homozygous DNA-samples contain only one of the two alleles which can be detected in only one of the two reactions, it is necessary to use two additional primers which produce the same control product in all reactions. This control products is different from the specific product in order to control the efficiency of the respective PCR of the other allele and to establish the absence of the respective allele. If a control product is present in the PCR product but no specific product of the allele is found, the sample is not likely to contain the allele tested for in the reaction. In this method, the presence or absence of two alleles must be established in two separate reactions and each individual PCR must comprise a control PCR.

*Biochem. Biophys. Res. Commun.* (1989), 160:441–447 proposes to increase the selectivity by decreasing the dNTP concentration. Even if this additional measure is taken, the detection of alleles in separate batches can yield non-specific products.

In a ligase chain reaction (LCR: WO 89/09835), thermostable ligase is used to specifically link two adjacent oligonucleotides. This occurs only if they are hybridized to a complementary target at a stringent hypridization temperature and if base-pairing at the site of linkage is complete. If two alleles differ from each other as a consequence of a mutation at the linkage site, the above condition of complete base-pairing is fulfilled for only one of the alleles. Two additional oligonucleotides, which are complementary to the first two, are then necessary to amplify the ligation product in the ligase chain reaction. To date, the detection of two alleles requires two reactions with at least six oligonucleotides, and the amplification product is detected with a radioactive label (*Proc. Natl. Acad. Sci. U.S.A.* (1991), 88:189–193).

From *Proc. Natl. Acad. Sci. U.S.A.* (1985), 82:1585–1588 and from *New England Journal of Medicine* (1987), 317:985 a method of detecting alleles is known which is based upon differential hybridization of "allele-specific" oligonucleotides (ASO) with the alleles. Two oligonucleotides, each 20 bp in length, for example, are synthesized. Each matches one of the two different alleles but has a mismatch to the other allele located in the middle of the oligonucleotide sequence. Discrimination between alleles is then possible by differential hybridization with labelled oligonucleotides. This applies to the analysis of both human genomic DNA and PCR products. Direct and discrete analysis of genomic DNA is also possible with this method but requires additional digestion and electrophoresis.

*Nucleic Acids Research* (1989), 17:2437–2448 and EP-A-0 333 465 describe a method of testing preamplified human genomic DNA for the presence of various alleles in a few additional PCR cycles by competition of allele-specific primers (competitive oligonucleotide priming= COP). The above described ASO-technique is the converted into a PCR technique. In the original ASO-technique, an error rate of 5% caused by cross hybridization is acceptable since a comparison of the signal intensities during corresponding controls allows an unequivocal interpreation of the results. In a PCR reaction, however, where the primers are allele-specific oligonucleotides, the error rate for a sample that contains only one of the alleles would after ten cycles amount to 12% if this error occurred in a reagent mixture where both alleles are amplified. Gibbs et al. could indeed demonstrate that primer competition increases selectivity, however, the area of interest of the genomic DNA was first amplified in a PCR and the analysis for the different alleles was then carried out in ten subsequent cycles. Two allele-specific primers and a complementary strand primer were used in these cyles and in two reactions one of the allel-specific primers was radioactively labeled. A selective detection of different alleles has been demonstrated for oligonucleotides of 12 to 16 bases in length whereas longer oligonucleotides yielded under the given conditions also non-specific products.

Methods that are based on differential hybridization can only be applied in certain situations and, moreover, are very complex and susceptible to interference. Also, preamplification is a procedural step during COP which investigators would like to eliminate.

It was an object of the invention to provide a simple method for the specific detection of variant nucleic acids which does not require digestion by restriction enzymes and allows amplifying the nucleic acids in one reagent mixture.

The subject matter of the invention is hence a method of detecting variant nucleic acids whose nucleotide sequences differ in at least one position (X). The method comprises three steps:

—reacting a set of oligonucleotides, whose nucleotide sequences differ in the position which corresponds to position X, with the nucleic acids to be detected under conditions sufficient for hybridization, —extending the oligonucletides that are added by hybridization using the nucleic acids to be detected as templates and —detecting the extension product, whereby the oligonucleotides of the set must also differ from one another in at least one other position (Y).

Other subject matters of the invention are a set of oligonucleotides, a reagent kit and various applications and uses of said method.

Similar or closely related nucleic acids in accordance with the invention are those whose nucleotide sequences are substantially identical but differ in at least one position of their nucleotide sequence. For the remainder of this application, this position is referred to as X. If the subject matter of this invention comprises several differences, they will be referred to as X1, X2, . . . XN. Such differences may occur, for example, as a consequence of point mutation (e.g. some bases are substituted dor others) or may be caused by deletions or insertions of one or several bases). Nucleic acids which resemble one another are usually termed alleles.

Important point mutations can be found, for example, in LDL receptors (*Arteriosklerosis* (1989), 9:1–8 to 1–13) or in the apolipoprotein-B-gene (CGG→CAG mutation of codon 3500: *Proc. Natl. Acad. Sci. U.S.A.* (1989) 86:587–591), in the gene of the reverse transcriptase of the HIV virus (A→T mutation in codon 215: *Science (1989)* 246:1155–1158) and in the β-globin gene in case of sickle cell anemia (A→T switch in codon 6). Moreover, similar nucleic acids are found in related organisms, for example, bacteria and viruses (serovariants). In the nucleic acids of some bacterial strains, a particularly great similarity is found in the sequence of their ribosomal genes and their rRNA. Variant nucleic acids as defined by the invention also include control nucleic acids which are similar to a nucleic acid to be detected. Position X is also referred to as a polymorphous site. The nucleic acids to be detected can be RNA or DNA. In the diagnosis of bacteria, rRNA has proven to be particularly suitable.

The term original target is used to designate the nucleic acid that is contained in the sample. The term product target refers to those polynucleotides that are a product of the use of original targets. Product targets are also used as target nucleic acids and are usually smaller than the originial target.

Any further mention of detection of two nucleic acids and/or alleles made in this document refers to embodiments which apply analogously to the detection of nucleic acids by means of suitable oligonucleotides regardless of the difference found at position X (e.g all possible alleles)

The term position refers to a defined site on the nucleic acid. Such a position may, for example, be occupied by a nucleotide.

Nucleotides are referred to as being complementary if regular Watson/Crick base-pairing is ensured (e.g. G-C, A-T or A-U). This complementary base-pairing leads to matches whereas non-complementary base-pairing leads to mismatches.

Any other base or base analog creating such base-pairing (e.g. 7-deaza-dGTP, dITP) is also referred to as being complementary.

For the realization of the method in accordance with the invention, the nucleic acids to be detected must be present in a form that is suitable for in-vitro reaction. The sample to be examined, e.g. tissue, individual cells or a cell-containing fluid, is digested in a known manner in order to break down the cell walls (e.g. thermal, enzymatic or chemical lysis or combinations thereof).

If the nucleic acids are not present as single strands, they are converted into this form in a known manner (e.g. by means of thermal or alkaline denaturing, enzymatic separation of the strands, or destabilization of the double strands under certain salt conditions).

The sample is then brought into contact with a set of oligonucleotides. The conditions selected are such that the oligonucleotides of the invention hybridize with the corresponding areas of the nucleic acids to be detected. This hybridization is generally known as annealing. Hybridization with irrelevant nucleic acids, i.e. those not to be detected, is avoided by selecting a suitable nucleotide sequence, length, temperature, adjuvants etc.

The number of different nucleotides in a set of oligonucleotides of the invention corresponds to at least the number of different nucleic acids to be detected. The detection of two different nucleotides hence requires at least two different oligonucleotides (and possibly complementary oligonucleotides). The oligonucleotides used have a preferred length of the less than 100 nt, more preferably 5 to 50 nt. Each oligonucleotide has one nucleotide sequence which, with respect to the area contiguous to nucleotide X, is so highly complementary that this oligonucleotide can hybridize with the nucleic acid to be detected. However, the sequences of one set of oligonucleotides in accordance with the invention exhibit very specific differences.

One difference in the nucleotide sequence of the oligonucleotides of one set can be found in the position which, after hybridization, corresponds to position X of the nucleic acid. This difference may be a consequence of a substitution by another base or base-analog or may be caused by deletion/insertion.

According to the invention, the term "match"-oligonucleotide refers to the one oligonucleotide, which has at position X a nucleotide that is complementary to the nucleotide found at position X of the nucleic acid to be detected. The nucleic acid (used for the extension) which matches said oligonucleotide is referred to as the target nucleic acid. The term "mismatch"-oligonucleotiderefers to an oligonucleotide whose nucleotide at position X is one that is not complementary to the nucleotide at position X of the nucleic acid to be tested.

Depending on which variant of the method in accordance with the invention is selected, nucleotide X is located at a given site of the oligonucleotides, for example in the middle or at the end of the oligonucleotides. In the first case, the process of the invention is an improvement over the process that is based on the principle of competitive priming (hereinafter referred to as variant 1). In the second case, it is an improvement of the mismatch-priming-method disclosed in EP-A-0-332 435 and related methods (hereinafter referred to as variant 2). However, regardless of the variant applied, each oligonucleotide used in the detection of a nucleic acid has a nucleotide which corresponds and is complementary to the nucleotide found at position X of the nucleic acid. At position X of this oligonucleotide, there, hence, exists a nucleotide which is not complementary to the corresponding nucleotides of the remaining nucleic acids which are contained in the sample and differ with respect to position X.

The oligonucleotides of the invention differ from one another in at least one more position Y. This can be achieved by substitution with other bases or base-analogs and/or deletions/insertions in the sequence of the oligonucleotide. At least one, preferably each of the oligonucleotides of a set in accordance with the invention, has at a position Y a nucleotide which is not complementary to the corresponding nucleotide of the nucleic acid to be tested. For an optimum performance of the method in accordance with the invention, it is essential that the location of positions Y of the oligonucleotides of a set are relatively different from the location of position X. For variant 1, the location of Y on the oligonucleotide is not of crucial importance. It may, hence, be freely selected.

In variant 2, the preferred location of position Y is in the vicinity of nucleotide position X at the 3' end of the oligonucleotides. Preferably, position Y is located 1–8, more preferably 1–3 nucleotides away from X. It has proven to be favorable, for example, if Y of the one oligonucleotide is the nucleotide following the terminal nucleotide (position X) and Y of the other oligonucleotide is the nucleotide found two or three nucleotides away from the terminus. In another oligonucleotide (for the detection of three similar nucleic acids), the non-complementary nucleotide could then be three or two nucleotides away from the terminal nucleotides, for example, and so forth.

For the remainder of this document, positions Y of the 1, 2 . . . N oligonucleotides of one set are referred to as Y1, Y2 . . . YN. Also, it is possible that nucleotides which match the definition of the nucleotide at position Y are found at more than one position of each oligonucleotide. Preferably, the oligonucleotide has 1–5 such nucleotides.

A preferred set of oligonucleotides used is, hence, one which has at least two oligonucleotides in accordance with the invention. These oligonucleotides must differ from one another in at least the nucleotides which correspond to X and in two other nucleotides. A consequence of this arrangement of non-complementary nucleotides in the oligonucleotides is that an extension product, which together with another oligonucleotide of the set has but one difference in the nucleotide in position X, is not produced in any phase of the subsequently carried out extension reaction, e.g. a PCR known from EP-A-0 200 362. Maintaining a second different nucleotide position is, however, of great importance as is known from EP-A-0 332 435. Oligonucleotides of one set have at least one common segment of nucleotide sequences which, except for position Y, is complementary to the common sequence of the nucleic acid to be tested. Preferably, these segments comprise more than 50% of the length of the oligonucleotides.

After hybridization of the oligonucleotides to the nucleic acid to be tested, the resulting hybrids are subject to an extension reaction. A preferred extension reaction of this kind is the addition of mononucleotides to the oligonucleotide in 3'- - - 5' direction. These mononucleotides are complementary to the corresponding nucleotides of the original target nucleic acid. An extension preferably occurs when the nucleotide of the hybridized oligonucleotide, said nucleotide being the terminal nucleotide in direction of extension, is complementary to the corresponding nucleotide of the one nucleic acid (match) and when its chemical structure allows an extension. The reaction conditions for extending such a chain by means of a polymerase and mononucleotides are known, for example, from EP-A-0 201 184 or EP-A-0 332 435.

Further, such an extension can also be effected by linking another oligonucleotide to the already hybridized match-oligonucleotide. The oligonucleotide to be hybridized must be essentially complementary to the single-stranded area of the nucleic acid which follows the segment to which the match-oligonucleotide is already hybridized. This type of extension can be effected in a ligase reaction. An extension reaction of this kind is described, for example, in *Proceedings of the Natl. Acad. of Sciences U.S.A.* (1991), 88:189–193 or in WO 89/09835. Other amplification processes to which the invention can be applied include the Repair Chain Reaction (WO 90/01069), the process of DE-A-4010465 and the first stage of the process known from WO 91/03573.

In variant 1 all oligonucleotides hybridized to nucleic acids to be tested are extended. However, since the mismatch-oligonucleotide P1 of the one nucleic acid has at least two mismatch-nucleotides (X, Y1), it hybridizes with this nucleic acid under competitive condition less well than the match-oligonucleotide P2 which carries the match-nucleotide at position X. This is based on the provision that position Y in the two competing oligonucleotides is selected such that their competition is still determined by the respective base present at position X (and not by the differences found at the Y positions). In variant 1, the oligonucleotides, when hybridized on the original target, may also be offset with respect to each other. However, positions X and, preferably, positions Y are preferably located in the common area. The main product of the extension reaction is hence a nucleic acid which is based on an extension of the match-oligonucleotide.

In variant 2, mismatch-oligonucleotides can hybridize to the respective nucleic acid to be detected. However, only the match-oligonucleotide is extended.

A prerequisite for the specificity of the extension reaction in variant 2 is that the enzyme effecting the extension reaction catalyzes an extension of the oligonucleotides, almost regardless of whether or not a mismatch is present. These prerequisites are fulfilled, for example, when *Thermus aquaticus*-DNA-Polymerase (EP-A-0 258 017) or *E.coli*-Ligase are employed.

The segment located between the outer ends of the oligonucleotides which are to be hybridized to the nucleic acids to be tested is amplified by reacting the resulting extension products with oligonucleotides which are essentially complementary (complementary oligonucleotides) and then allowed to hybridize. These oligonucleotides are extended with the aid of the extension products as templates obtained in the first step. Position X is ususally located in the segment of extension. The complementary oligonucleotides can be identical for all nucleic acids to be detected but may also be allele-specific.

This extension, too, can be effected by adding mononucleotides or oligonucleotides.

When the oligonucleotides of the invention, which differ from one another not only in position X but also in two additional positions, the second extension reaction (hereinafter referred to as cycle 2) yields a product, which, with respect to all other oligonucleotides except the one from which it was obtained by hybridization and extension, has at least 3 (i.e. more than there were originally) non-complementary nucleotides. This makes an extension of mismatch-oligonucleotides at this point more difficult. Analogously, additional Y positions render erroneous annealing to the amplification product of the respectively other allele more difficult. Any blocking of the amplification product of the matching oligonucleotide and, hence, reduced yield are thus obviated.

These improvements of the known methods are subsequently explained with reference to FIGS. 1 to 4.

The main product of the extension reaction of variant 1 is a nucleic acid which is based on the extension of the match-oligonucleotide. Hybridization of the mismatch-oligonucleotide to an extension product from cycle 2 of the hybridization with the match-oligonucleotide is practically impossible since there exist already three mismatches (X, Y1, Y2). This situation is demonstrated in the example of FIG. 1. A successful result is practically achieved by selecting a suitable annealing temperature (if desired, other reaction parameters such as oligonucleotide concentration may also be employed).

Heating up to 90° C., for example, subsequent cooling down slowly to a temperature just above the $T_M$-value of both primers on the original target, followed by a slow cooling to a temperature significantly below the $T_M$-value of both primers ensures that the allele-specific primers hybridize to the target which matches best. The $T_M$-value is defined as the temperature at which 50% of a target sequence are hybridized with a primer. At this temperature, a bound matching oligonucleotide can also be rapidly released again (equilibrium). The $T_M$-value for an oligonucleotide that matches less well is lower on the same target. This means that at this low $T_M$-value, the oligonucleotide that matches less well is not likely to bind to said target but will be displaced by the matching oligonucleotide now binding more than 50%. Both alleles undergo annealing when temperatures are appropriate. As compared to the $T_M$-values of the oligonucleotide/target combination [(A), (B), (C), (D) FIG. 1], the $T_M$-values for the perfectly complementary target combination [(E), (H), FIG. 1] are significantly elevated since mismatching caused by additional mutations during amplification of the PCR product, lowered the $T_M$-values for the former combination. As opposed thereto, the $T_M$-value for the oligonucleotide/PCR-product target combination where one oligonucleotide hybridizes with the non-matching allele [(F), (G), FIG. 1] is again significantly lower than the value found for the original target since the additional mutations from both oligonucleotides selected in accordance with the invention accumulate. Specificity of amplification of the PCR products is hence again increased. If the temperature selected for the annealing in the PCR lies just below the $T_M$-values of the perfectly complementary combination, incorrect annealing to the PCR products (F), (G) or to the original templates (B), (C) is practically excluded. The advantage of variant 1 over the known COP process lies in that it requires no or only an approximate differentiation by means of temperature control in the follow-up cycles. Moreover, genomic nucleic acids can be detected without preamplification.

The presently described variant is particularly suited for multiplex analyses. In the annealing step which precedes the PCR not only the $T_M$-values for a mutation and the corresponding primers are obtained but all oligonucleotides can also selectively anneal since they are allowed to cool down slowly within a certain range. This range begins above the highest $T_M$-value and reaches below the lowest $T_M$-value.

The second variant is explained with reference to FIGS. 2–4. This variant where the 3'-terminal nucleotide of the oligonucleotides corresponds to position X is preferred since it has a higher selectivity. This is due to the fact that because of its higher selectivity, it often does not matter whether the mismatch oligonucleotide hybridizes or not.

This principle can be illustrated with the following example. One single reaction vessels contains a reagent mixture for a PCR for the simultaneous detection of two alleles of one gene. These alleles differ in one base position (where base M(utant) is found in one allele and base N(ormal) in the other). Three primers, one complementary primer and two primers each selective for only one of the two alleles, are used in the reaction. Primer selectivity is effected in that the base at the 3'-end of the one selective primer is complementary to M, the base of the other primer is complementary to N. The two allele-seletive primers are distinguished, for example, by two additional substitutions whereby one template mismatch is created in each primer so that each of the two primers has one mismatch to the respectively selective allele and two mismatches to the other allele. Moreover, in order to distinguish easily between the resulting PCR products, it is possible, for example to select allele-specific primers of different lengths. These alterations are incorporated in the respective PCR products so that in the course of the PCR, its product resulting from one of the allele-selective primers consitutes, as compared to the original target, an improved (i.e. completely complementary) target for this primer. Moreover, it no longer is a suitable target for the other allele-selective primer since the primer now has three mismatches with respect to the altered target. Incorrect allele selection by the primers is hence essentially based in the annealing to the original target and/or in the subsequent extension of the primer. Because of the additional alterations, the subsequent amplification of the available PCR products occurs separately.

FIG. 2 shows the realtive position of the oligonucleotides used in the examples (position 1 at the 3'-end). The example refers to the detection of two alleles of the apolipoprotein-B-gene (*Proc. Natl. Acad. of Sciences U.S.A.* (1989). 86:587–591).

Additional differences at the Y-positions at position 28 (Y3:C, mismatch) and position 29 (Y4:C. mismatch) of P2 were included in oligonucleotides P1 and P2 to further separate the amplification of the individual alleles in one reaction. In the following, the terms match and mismatch refer to the sequence of the normal allele.

oligonucleotide P1: Asa short (29 bases): SEQ ID No. 1
    nucleotide at position X: T (selective mutant) nucleotide at position 2 (Y1): G (mismatch) nucleotide at position 4 (Y2): G (match)

oligonucleotide P2: Asa long (49 bases): SEQ ID No. 2
    nucleotide at position X: C (selective normal) nucleotide at position 2 (Y1): C (match) nucleotide at position 4 (Y2): T (mismatch)

oligonucleotide P3: complementary primer: SEQ ID No. 3 completely complementary to strand oligonucleotide P'2: Asa long (49 bases): SEQ ID No. 4 nucleotide in position X: C (selective normal) nucleotide in position 2 (Y1): G (mismatch) nucleotide in position 4 (Y2): G (match)

FIG. 3 shows the results of the first three cycles of a PCR provided oligonucleotides of the invention P1 and P2 are used for amplification in one reagent mixture. The last base at the 3'- end of oligonucleotide P1 matches the mutant allele, and the last base at the 3'-end of oligonucleotide P2 matches the normal allele. Consequently, the primer of the primer/template combination marked (B) and (C) in FIG. 3 is extended. The nucleic acids (F) and (G) are the products of this reaction. The differences (mismatches) marked with an asterisk (*) in (B) and (C) do not completely prevent the extension of the primers. During the second PCR-cycle, strands ((I) and (K), upper sequence) are formed which are exactly complementary to the extension products. These newly created products may hybridize with the respective other oligonucleotide to form products (O) and (L) but because of the 3 mismatches present in these hybrids no extension reaction takes place. An extension reaction does however take place with the corresponding oligonucleotides from products (M) and (N).

FIG. 4 demonstrates that if oligonucleotides P1 and P2 are different, positions Y of the non-complementary nucleotides must not be identical since a secondary reaction otherwise greatly reduces target sensitivity. In the case shown in FIG. 4, each of the two oligonucleotides P1 and P2' have a mismatch in the first two positions at the terminus in direction of extension. It is obvious that the PCR products formed in the second cycle have but one single mismatch to the respective other oligonucleotide (products O and L). An extension of these products can reduce specificity since the products have only one mismatch. With the known processes, it would hence not be possible to determine both alleles in one reagent mixture with sufficient specificity.

In variant 2, specificity of detection can be further increased by additional differential hybridization of the oligonnucleotides to the nucleic acids as known from COP. In the presently described embodiments of variant 2, the oligonucleotides hybridize with all nucleic acids to be detected with approximately the same efficiency. If, however, the oligonucleotides show additional differences in position Y (e.g. mismatches), specificty and yield of amplification can be increased by selecting an appropriate temperature for the hybridization of the oligonucleotides to the nucleic acids to be detected in, for example, a PCR (temperature is just below the $T_M$-value of the hybrid consisting of nucleic acid to be detected and corresponding oligonucleotide). The location of these additional Y-positions is not restricted to a certain segment, for example, near the 3'-end, but can be freely selected at any position in the oligo. The definition of the Y-position is the determining factor to distinguish between the oligonucleotides. The alterations in each oligonucleotide are incorporated in the respective match product and the corresponding product of the compelementary strand and, when an suitable temperature is selected, they make it more difficult for the respective other oligonucleotide to anneal to a wrong product target. It is therefore hardly possible that a mismatch-oligonucleotide interferes with the annealing of a match-oligonucleotide to the product. Amplification hence occurs separately and a reduction of the amplification rate by interfering incorrect annealing is excluded.

In additional embodiments, especially of variant 2, two or more nucleic acids having two or more alterations (polymorphous sites, X1, X2, . . . XN) can be detected in the nucleotide sequence. The method described in (*Nucl. Acids Res.* (1988). Vol. 16, 23:11141–11151) can be employed (Muliplex Process) analogously.

The invention proposes several possibilities. In a first embodiment, the polymorphous sites are independent subject matter of the invention. The invention uses as many oligonucleotides as there are polymorpous sites to be detected on the various nucleic acids. Two polymorphous sites on two nucleic acids hence require the use of a set of 4 oligonucleotides of the invention P1, P2, P4, P5. Such a case is shown in FIG. 8. The amplified areas which are also restricted by the two primers of the complementary strands, do not overlap but preferably have different lengths. This allows a seaprate detection. Alternatively, it is possible to omit primer P6. Then, complementary strand primer P3 is used in the amplification for both polymorphous sites.

A second embodiment is based on the principle that the sets of oligonucleotides of the invention which belong to different sites will hybridize with different strands of the nucleic acids to be detected (FIG. 9). In this example, it is possible that the amplified segments overlap whereby analogous use of the Y-positions (in the overlapping segments of oligonucleotides P1, P2, P4 and P5) ensures that the amplifications of both polymorphous sites occur separately. This case, too, requires four oligonucleotides (P1, P2, P4 and P5) and two complimentary strand primers.

In a third preferred embodiment (FIG. 10) where the detection processes of several polymorphisms are coupled, complementary strand primers are not required since the oligonucleotides of the invention act as such. This is a simple way of forming and detecting four different amplification products depending on the presence of corresponding alleles. Direct determination of the cis/trans-location of mutations is hence also possible.

Analogously, the above embodiments can also be used for more than two polymoprphous sites.

A particularly preferred embodiment employs a PCR (EP-A 0 201 184) to which reference is made in greater detail in the following. The detection of variant nucleic acids requires the substitution of a primer by a set of oligonucleotides in accordance with the invention. The remaining reaction conditions for the amplification, especially the use of the complementary strand primer, apply analogously.

The Ligase-Chain-reaction (LCR, EP-A-0 320 308) can also be improved in accordance with the invention. Instead of at least one oligonucleotide, this improvement uses a set of oligonucleotides in accordance with the invention. FIG. 13 demonstrates that the number of mismatches in cross products is increased.

Depending on the location of Y, the extension and/or annealing of incorrect oligonucleotides is largely suppressed. In this embodiment, position X may be located at the 3'-end of the one oligonucleotide or at the 5'-end of the other oligonucleotide. In principle, an LCR where X is located the the middle of the oligonucleotide can be carried out analgously to COP process. Preferred are those complimentary strand oligonucleotides whose nucleotides loctated at positions that correspond to Y are not complemetary to any of the nucleotides at the Y positions of the oligonucleotides of the invention.

It is, however, also possible to use the improvement in accordance with the invention in promoter-primed, cyclically arranged amplification reactions as is known from the processes of EP-A 0 310 229, EP-A-0 329 822 or EP-A-0 373 960. Reference to the contents of these documents is now made. In these amplification processes, a promotor primer serves to form a multitude of product targets (RNA) which are again amplified with the aid of the promotor primers.

The specific detection of the extension products, which is a measure for the presence or the quantity of the nucleic acid to be detected in the sample is, for example, also possible by making use of the fact that the oligonucleotides used are discriminated by one more feature. Such a distinction could be, for example, the varying lengths of oligonucleotides of one set. The extension of different oligonucleotides then produced products of different length. The oligonucleotides can further be distinguished by having differently detectable groups D. Such detectable D groups are, for example, color or fluoresence molecules or chemical groups which can be detected in a subsequent reaction with the aid of a detectable group D. Chemical groups of this kind include, for example, haptens such as digoxin and digoxigenin. Haptens can be detected by reacting them with a labeled antibody to the hapten. The label is then detected. Another hapten could be biotin, for example, which can be detected by using a differently labeled antibody or straptavidin.

The various extension products which are a measure for the quantity and the presence of the nucleic acid to be detected can be detected in various ways. They can be separately detected after separating the reagent mixture or sequentially once the reagent mixture is obtained or, provided appropriate labels are used, simultaneously according to known methods. The method described in EP-A-0 324 474 has proved to be the preferred method for the use of steroid hormones as markers. Another method is the use of different fluorescent dyes. The oligonucleotides can either be labeled directly or antibodies to chemical groups can, for example, be provided with corresponding fluorescent labels. The various allelic product can be detected by simultaneously measuring the fluorescence in several channels. Also, part of the products can be labeled with fluorescent labels whereas enzymes can be used for other products from the same reagent mixture. In principle it is possible to employ any known method of labeling and detecting.

In a sequential or simultaneous detection, the two different chemical groups, preferably haptens which are detected by different antibodies, can be used, for example, to label the two oligonucleotides. Such haptens include digoxigenin, biotin, and fluorescein. Preferably, the antibody to fluorescein and the antibody to digoxigenin then have different enzymes as labels. The nucleic acids are then detected by sequential or simultaneous contact with enzyme-specific detectable substrates. Alternatives for the detection of extension products are given in FIGS. 5 to 7.

The mixture of the common extension reaction is subject to the denaturing reaction of the embodiment shown in FIG. 5 (left). A capture probe is used to bind the single-stranded extension products to a solid phase (F) which is immobilized or can be immobilized via a group I (e.g. biotin). In this procredure, the extension products of the reaction are immobilized together with all nucleic acids to be detected. Due to the various detectable groups the nucleic acids can be detected sequentially (separated by a washing step). If the signal to be detected can be produced and detected at the same time in one vessel, such a washing step can be omitted.

In the variant shown on the right side of FIG. 5, at least two (or correspondingly more if detection involves more than two allels and if more than two labeling enzymes are used) sufficient aliquots of liquid are taken from the reagent mixture after the extension reaction has occurred, and each aliquot is tested for extension products. The aliquots are taken from a multiplex reaction, and depending on the number of different labels used for the oligonucleotides, a corresponding number of amplification products can be detected in each aliquot.

FIG. 6 also shows a method where a mononucleotide or an oligonucleotide modified with an immobilized group was incorporated during the extension reaction. The extension products can then be directly (i.e. without separate capture probe and without denaturing) bound to a solid phase (corresponds to DE-A-4001145). As shown in FIG. 5, simultaneous, sequential or parallel detection is possible.

The embodiment of FIG. 7 is based on the fact that, preferably, the extension products for various nucleic acids to be detected differ from one another in at least three nucleotides. This fact is used for a selective immobilization with a capture probe. Detectable groups D are introduced by incorporating a modified mono-or oligonucleotide. This group can be identical for the extension products of both alleles. If the amplification of the nucleic acid was carried out as specified in variant 2, the alterations Y are located in the vicinity of X and the capture probe can be selected so as to be identical with a part of the oligonucleotide sequence and with a part of the extension sequence. This serves at the same time to select the correct extension product (artefacts are lacking the extension sequence) and the various alleles.

Other conceivable embodiments include selective immobilization via incorporated oligonucleotides. For each allele, these oligonucleotides have another immobilizable group. Detection is then carried out via incorporated detectable mononucleotides, an incorporated detectable mononucleotide or with a detection probe.

When oligonucleotides of different lengths are used, a preferred detection method is the separation of extension products, which have the same length as the amplified area (including the oligonucleotides), via gel chromatography. Detection is then carried out immediately after separation in the gel (e.g. ethidium bromide dye), after incorporation of labeled oligonucleotides, mononucleotides or after hybridization with labeled probes. Electrophoretic mobility can also be altered, for example, by labeling an oligonucleotide with biotin at the 5' end. Following amplification, an aliquot of the product is incubated with streptavidin; the binding of the streptavidin to the biotin-labeled significantly reduces the electrophoretic mobility of the whole product whereas the other product maintains its normal mobility.

If one of the variant nucleic acids is not contained in the probe, the signal generated by extending the corresponding oligonucleotide is, preferably, not measured for this nucleic acid. The method of the invention can hence also be used to detect only one of the variant nucleic acids or to determine the absence of all nucleic acids.

Since the extension product from one allele does not cross-react with the oligonucleotides used to detect the other allele, it is possible to detect the variant nucleic acids simultaneously in one reagent mixture and in one single reaction vessel. The reaction is not optimal when the non-complementary positions Y (mismatches) are identical with the nucleic acids for various oligonucleotides.

The method of the invention is employed in a variety of applications. It is possible, for example, that the alleles of a probe obtained from one single test subject (individual diagnostics) are related to certain diseases (e.g. metabolic disorders).

Moreover, because of its good specificity, the method is also suited for assays where probes are subject to pool-screening. According to this principle a great number of individual probes of different test subjects is mixed. When diagnosing the defect in the apo B 3500-gene, it has proven to be suitable to combine 64 probes in one pool. With the method of the invention it is possible to determine the presence or absence of this defect in a probe contained in the pool. When several partial pools from a pool with positive results are successively tested several times in accordance with the method of the invention, a small (as compared to prior art) number of determinations suffices to detect the gene which bears the defect.

In the method of the invention it has proven to be particularly advantageous to simultaneously detect the gene that does not bear the defect provided this gene is present. When screening a pool, it is possible to alternatively detect the mutant product or, if no mutant allele is present, to detect the normal product. In addition to its function as a control for the reaction as such, the detection of both alleles is also a means of quantifiying the nucleic acids to be detected.

Since the samples used in pool-screening methods are not patient-specific but anonymous, these methods can be used in the testing of diseases which are of particular epidemiologic relevance, for example, the contamination rate of the AIDS virus or, for example, the frequency of elevated cholesterol levels, hypertension or diabetes (mass screeening). These methods serve to determine the frequency of alleles.

The same applies to the species diagnostics of bacteria and, in some cases, to virus diagnostics. The area of particular interest focusses the simultaneous detection of closely related pathogenic/non-pathogenic species or strains. Further, the method of the invention is also suited to reliably detect *E. coli* K12 (evaluated in accordance with law of genetechnology) via the kwown AT-sequences whereby various strands of *E. coli* are distinguished. The method can hence also be applied in analysis of environmental conditions.

The main advantage of the invention over prior art is the possibility of simultaneously detecting allelic compounds in mixtures contained in one single vessel with practically no relevant secondary reactions. Digestions with restriction enzymes is not required. This object is achieved by virtue of the fact that the amplification processes of the individual alleles occur quasi separately (cross reactions are reduced) although they all take place in the same vessel.

Another subject matter of the invention is a set of oligonucleotides which contains at least two oligonucleotides suitable for hybridizing with similar nucleic acid. These oligonucleotides must differ in at least two, preferably 3 defined positions and, preferably, in one more structural feature. Preferred oligonucleotides are those where the differences are found in the nucleotides of the 3'-end (corresponding to position X) and in two more nucleotides and which are distinguished by another structural difference. The detectable structural difference can be the different lengths of the oligonucleotides or a detectable or immobilizable group. The oligonucleotides can be present as a mixture. Further, this mixture can contain additional oligonucleotides required for the amplification of nucleic acids with the aid of the set of oligonucleotides of the invention; they include, in particular, complementary strand oligonucleotides and primers.

The intended effect of the invention is also encountered in oligonucleotides where the nucleotides of position Y differ from one another and are not complementary to the nucleotides of the template nucleic acids if the distance of this position Y to X is the same in the oligonucleotides of this set. The effect is diminished in a set of oligonucleotides of which only one has a nucleotide at position Y that is not complementary to the corresponding nucleic acid. The set of oligonucleotides in accordance with the invention is used to accomplish the object of the method in accordance with the invention.

Another subject matter of the invention is a reagent kit for the detection of nucleic acids. Said kit comprises a set of oligonucleotides in accordance with the invention and, if necessary, additional oligonucleotides and adjuvants necessary for the extension of the oligonucleotides. Further, the reagent kit can comprise additional oligonucleotides, for example, complementary strand primers. Preferably, the kit provides the enzyme and the oligonucleotides and the other reagents in separate containers.

Yet another subject matter of the invention is the use of the process of the invention for the simultaneous determination of alleles in one probe (e.g. the typing of transplant antigens on DNA basis), the simultaneous determination of topologically closely related infective agents (in patient monitoring, therapy control) and the use in the screening of pools of probes for the presence of closely related nucleic acids or their frequency. Further, the use of the method for the detection of mutations is also

Figure 1:
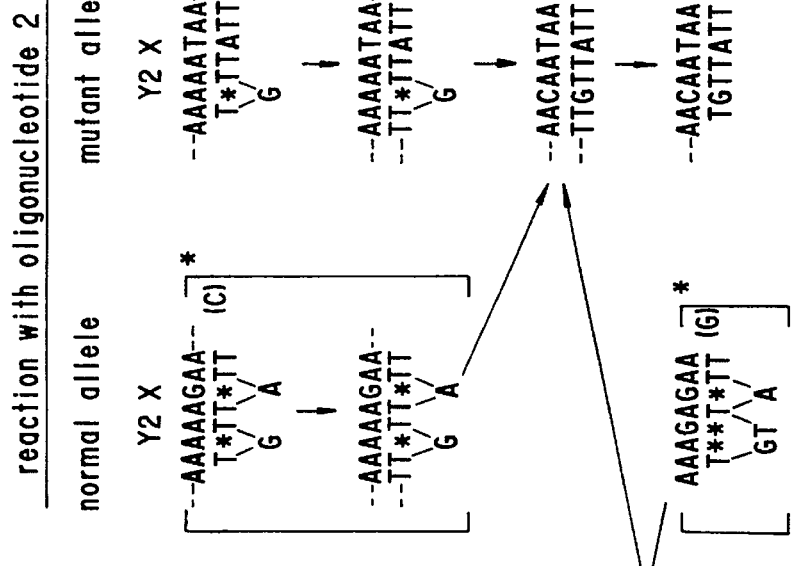
FIG. 1 shows, in theoretical form, a method in accordance with the invention which is based on competitive priming.
Figure 1:
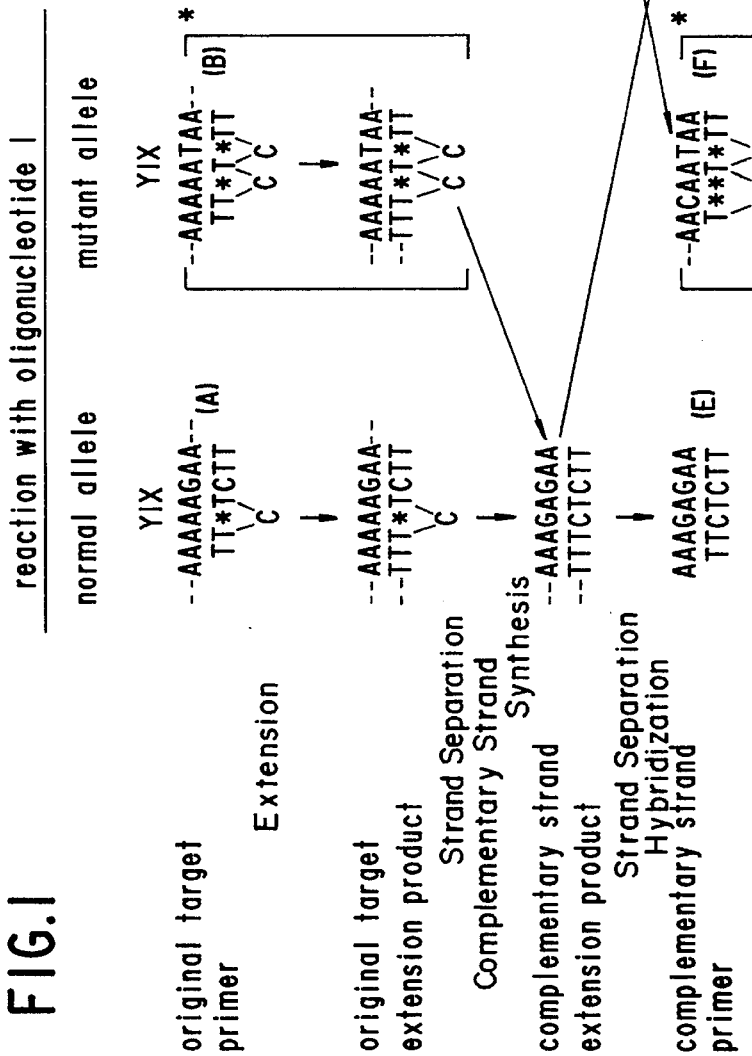

| List of references | |
|---|---|
| I | immobilization group |
| D | detection group |
| D1, D2 | various detection groups |
| F | solid phase |
| P1, P4 | primer 1, 4 according to the invention |
| P2, P5 | Primer 2, 5 according to the invention |
| P2' | reference primer |
| P3, P6, P7 | complementary stand primer |
| X, X1, X2 | allelic positions |
| Y1, Y2 | position of mismatches |

The following examples are given to illustrate the invention.

EXAMPLE 1

Detection of both alleles with respect to the CGG→CAG-mutation in codon 3500 of apolipoprotein gene in one reaction Sample preparation Human genomic DNA was isolated from EDTA-blood after the Higuchi method (in: *PCR Technology, Principles and Application For DNA Amplification.* (1989). published by H. A. Ehrlich, Stockton Press, New York), pp 31–38). The final volume of DNA solution corresponds exactly to the volume of EDTA-blood used. An average of 7500 leukocytes/µl yields, for example, a 2 µl probe which contains up to 15 000 leukocytes. Up to 100 ng DNA are, hence, expected to be found in 2 µl solution. Once the method after Higuchi was completed, the DNA was heated up to 100° C. Another denaturing step preceding the PCR is thus no longer required.

Amplification in accordance with the invention with the aid of a PCR

The PCR of EP-A-0 200 362 was carried out in 0.5 ml tubes (Sarstedt No. 72699) using a GENE-ATAQ-Controller (Pharmacia). The reagent mixture was composed as follows:
dATP, dGTP, dTTP, dCTP: 10 µM of each
1 mM Mg Cl$_2$
6 µl 10×PCR buffer without Mg$^{2+}$
0.6 µl Asa short (primer P1; 95.7 ng/µl), SEQ ID NO 1
1 µl Asa long (primer P2; 81 ng/µl), SEQ ID NO 2
0.6 complementary strand primer P3 (92.4 ng/µl), SEQ ID NO 4
0.3 µl Taq-polymerase (5 units/µl, Beckmann)
60 µl total volume The 10×PCR buffer consists of the following: 100 mM Tris-HCl pH 8.3, 500 mM KCl, 0.1% gelatine Temperature intervals
45 times (1 min. 95° C., 1 min. 65° C., 1 min. 72° C.)
4 times (2 min. 65° C., 1 min. 72° C.)
once (5 min. 72° C.)
Cool down to RT Detection of extension products 10 µl of the PCR products were subsequently mixed with µl application buffer (40% sucrose, 0.25% bromophenol blue, 0.25% xylene cyanol, 0.1 M EDTA pH 8.0) and electrophoresed in agarose gel. The gel was composed of 3% NuSieve GTG (FMC/Biozym), 1% agarose NA (Pharmacia), 1×TAE, 0.5 µg/ml ethidium bromide: (50×TAE=242 g Tris Base, 57.1 ml glacial acetic acid, 100 ml 0.5 M EDTA pH 8.0). The gels run for 0.5–1 h at appr. 5 V/cm. Fluorescence was photographed at 300 nm using a Polaroid 667 black & white instant film with Camaq Reprostar equipment. Then, the picture was evaluated.

Figure 11:
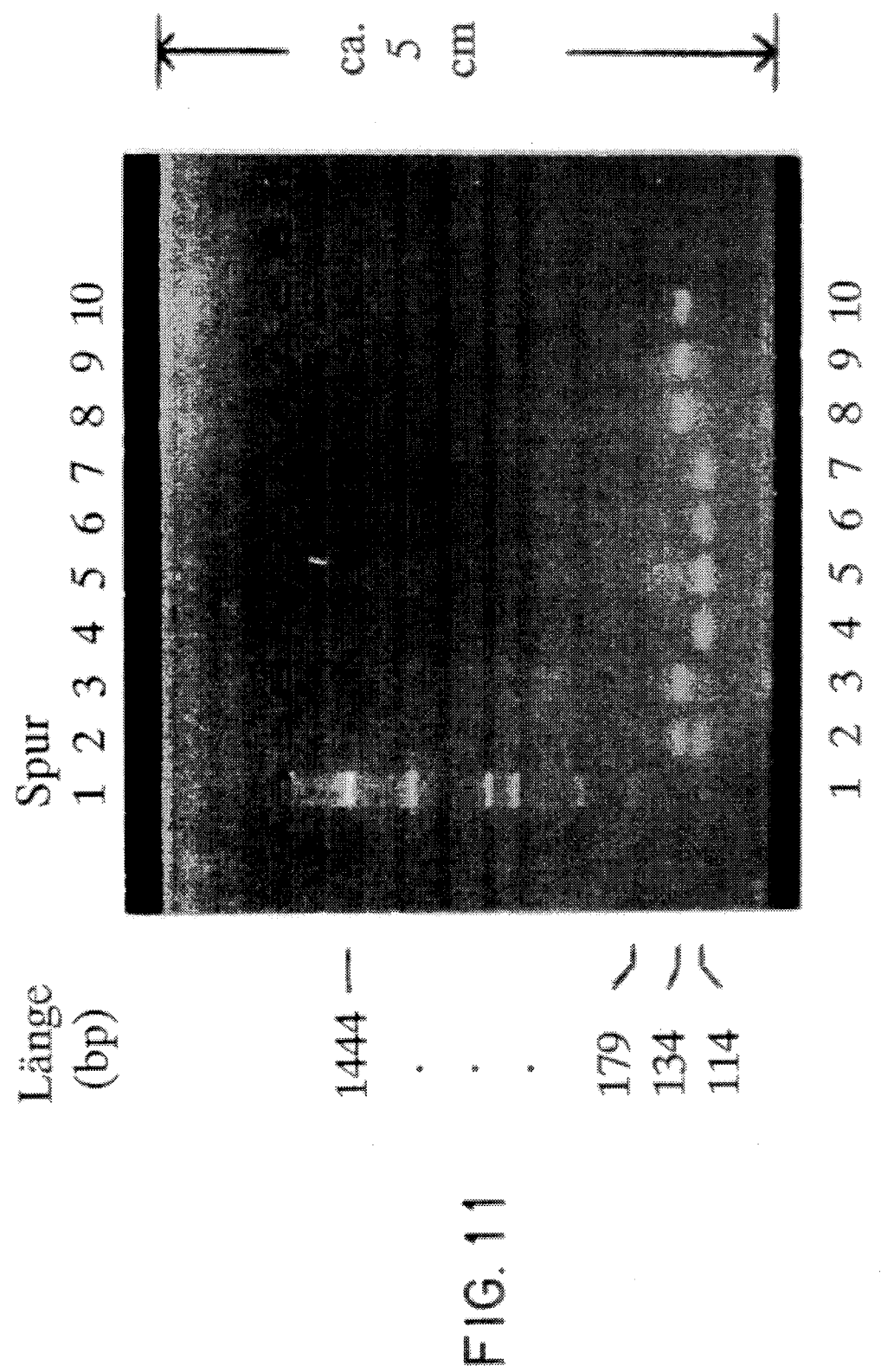
FIG. 11 shows an analysis of the probes amplified in example 1.

The following probes were analyzed (cf. FIG. 11) to demonstrate that a definitve identification of alleles requires the two allele-selective primers:
 1: standard of length
 2: heterozygous female test subject
 3: homozygous normal male test subsject and
 4: cloned mutant allele, quantity (molar) corresponding to probe 3

The probes were amplified with the aid of the two allele-selective primers P1, P2 and the complementary strand primer P3. As expected, the normal probe yielded a 134 bp product and the mutant probe only a 114 bp product. As compared thereto, the heterozygous femal test subject (lane 4 in FIG. 11) yielded both products as expected. The use of only one of the allele-specific primers produces a PCR product whose length corresponds to the one of the primer regardless of which template was amplified. Thus, especially the normal male test subject produces the band (lane 6) which corresponds to the mutant allele and the cloned mutant DNA generates the product of the normal selective primer (lane 10). Under the given test conditions, amplification according to the original ARMS - concept (C. R. Newton et at. (1989). *Nucleic Acids Research* 17:2503–2516) is in this case not suitable to discriminate between the alleles. Only the use of the presently described invention allows in the present case a correct and definitive (lane 2, 3) determination of the genotype and, moreover, both alleles can be determined in one reagent mixture.

The cloned DNA is a fragment which comprises positions 10573–1070 of the Apo B cDNA sequence in vector Gem3zf(–) (Atlanta/Promega). Before including the DNA in the PCR reaction, it was linarized with BamH1 and diluted to 0.06 pg/µl. This diluted portion contains appr. 15000 DNA molecules/µl. This means 2 µl thereof contain the Apo B sequence in appr. the same amount as do 2 µDNA solution of isolated DNA from EDTA blood.

These experiments demonstrate that the development of non-specific products, which occur although the reactions were carried out in separate vessels and supported by additional measures so as to increase specificity, can be suppressed when oligonucleotides in accordance with the invention used in one reaction vessel.

EXAMPLE 2

Screening for the CGG→CAG mutation in codon 3500 of the apolipoprotein B gene (pool screening)

This example shows that the method described here is suited for the detection of a carrier allele in a pool with DNA from other test subjects. Sensitivity was checked first. To do this, DNA obtained by isolation according to Higuchi (see example 1) was mixed as follows:
herterozygous DNA:normal homozygous DNA
1:50, 1:100, 1:200, 1:400, and 1:800
2 µl of the so obtained DNA solution were amplified in three reaction steps.

1st reaction step

In this pre-reaction, only the normal-selective primer was used to reconvert the DNA that was denatured during preparation. Single-stranded DNA was, hence, converted back into its double-stranded form. Incorrect priming of the great excess of normal alleles by the mutant-selective primer, which would occur because of the low starting temperature for the PCR, is thus obviated. This pre-reaction ensures that the mutant-selective primer encounters single-stranded normal templates during the subsequent reaction steps only at the desired annealing temperature. Because of the relatively small total volume of only 12 µl, the concentration of dNTP in this pre-reaction is relatively high since the total amount necessary for the 2nd reaction step was already included in this reaction step. A complete conversion of the single-stranded normal allele into a double strand is thus easier to realize.
2 µl DNA solution
10 µl aliquot of reagent mixture
 1.4 µl dNTP Mix (20 µM stock solution)
 0.9 µl Mg$^{2+}$ (20 mM stock solution)
 1.2 µl 10×PCR-buffer without Mg$^{2+}$ (cf. example 1)
 0.28 µl primer Asa long (81 ng/µl stock solution) SEQ ID NO 2
 5.99 µl H$_2$O
 0.23 µl Taq-polymerase (5 U/µl, Beckmann)
12 µl total volume
Temperature intervals: 4×(2 min 60° C., 2 min 72° C.), 5 min 72° C., no oil was applied.

2nd reaction step

Figure 2:
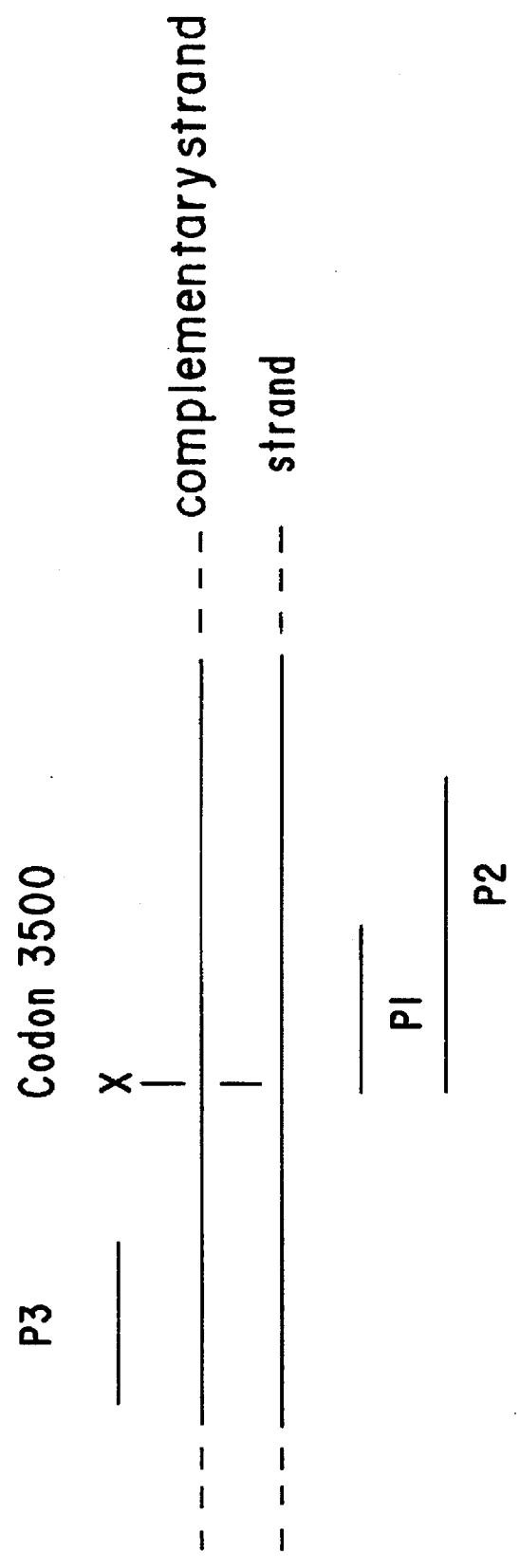
FIG. 2 shows the arrangement of the nucleotide sequences as used in FIG. 3 and the examples.
Figure 3:
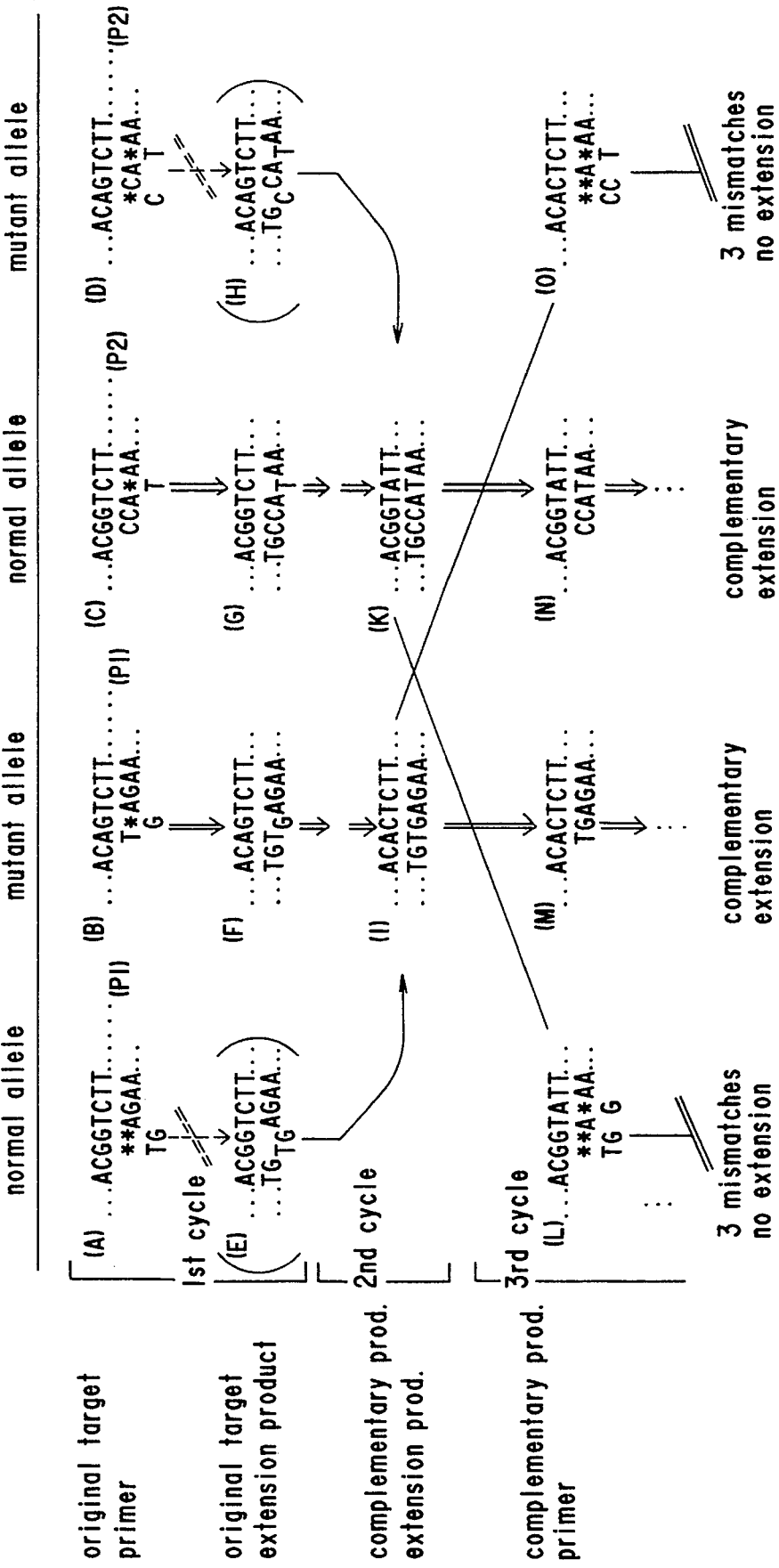
FIG. 3 shows the method in accordance with the invention for the use of 3'-mismatch oligonucleotides.
Figure 4:
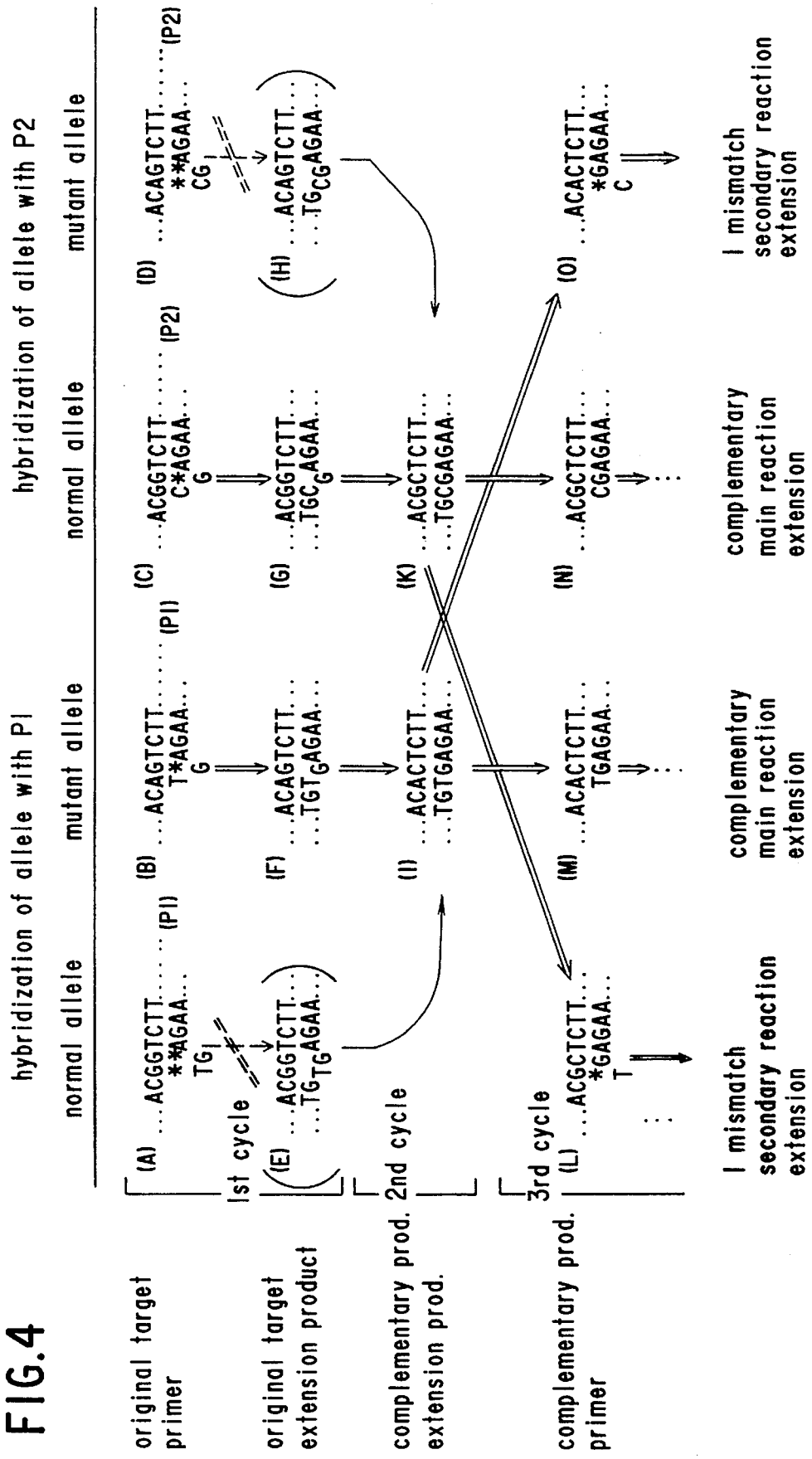
FIG. 4 shows a method where the mismatch-nucleotides are both located at the same position near the end of the oligonucleotides.
Figure 5:
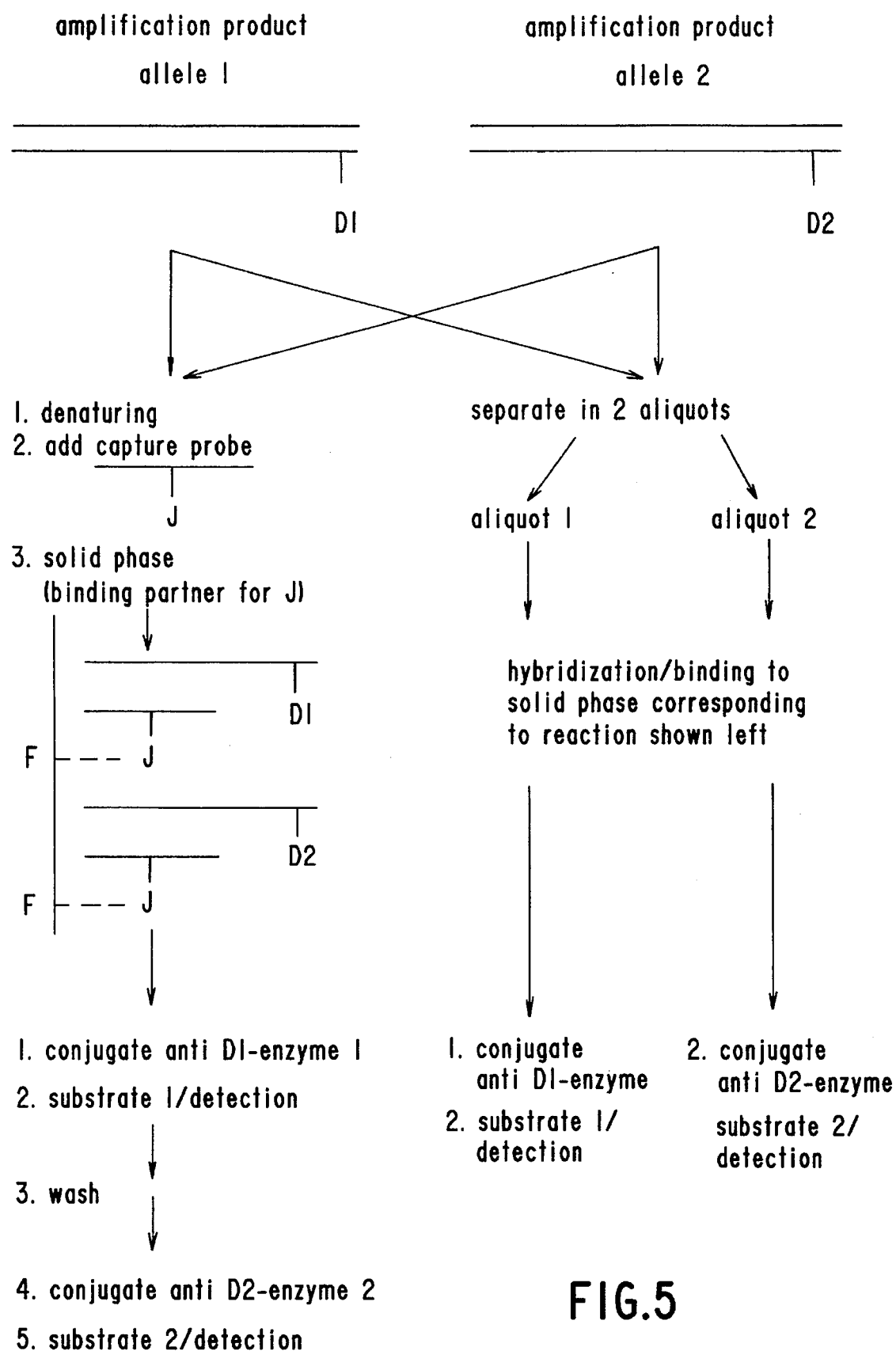
FIGS. 5 to 7 show embodiments for the detection of the extension products of the method in accordance with the invention.
Figure 6:
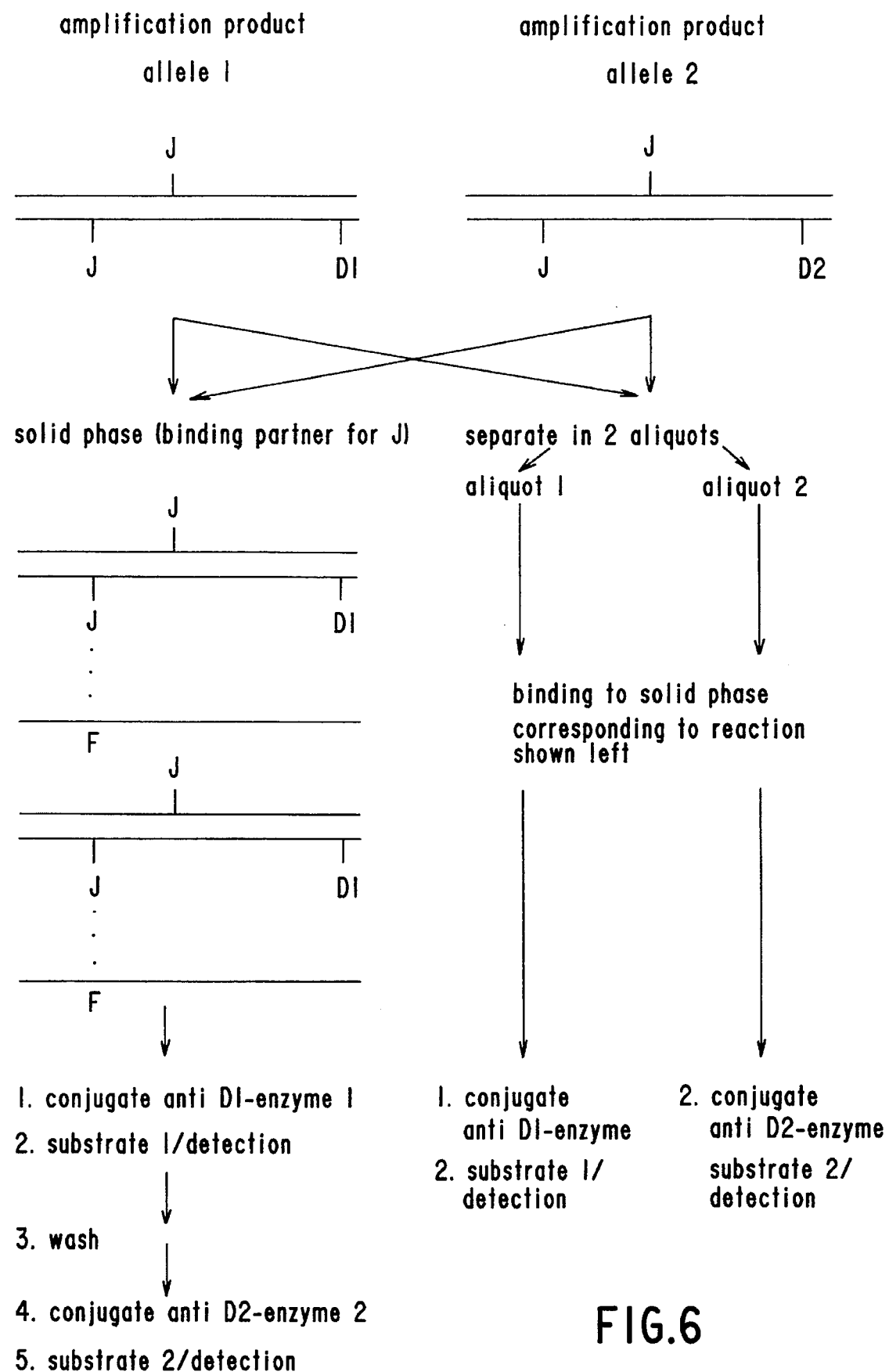
Figure 7:
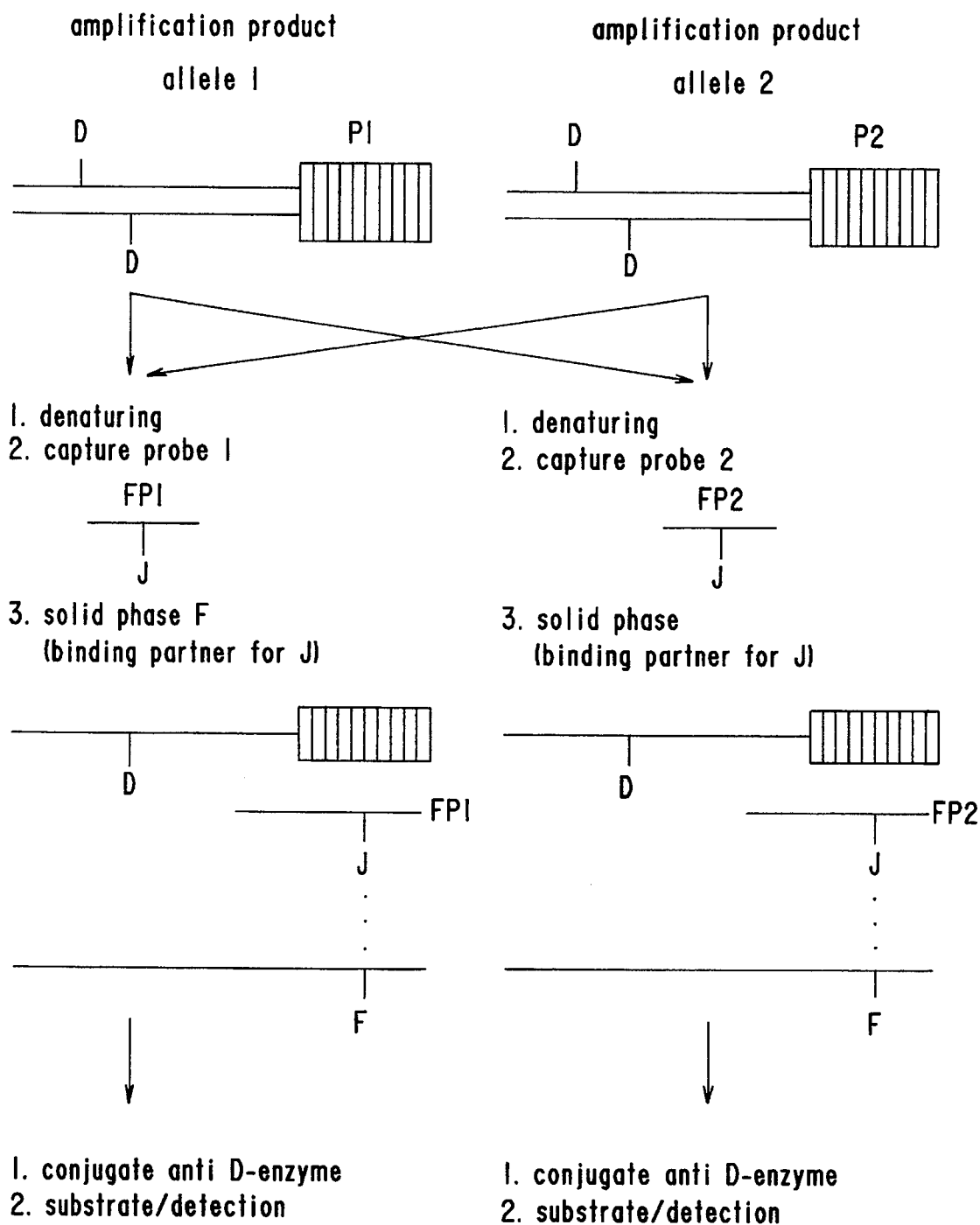
Figure 8:
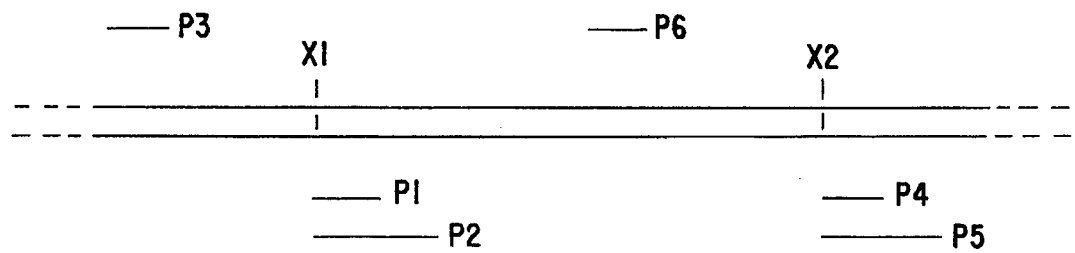
FIGS. 8 to 10 show the method of the invention as used for the simultaneous detection of several polymorphous sites.
Figure 9:
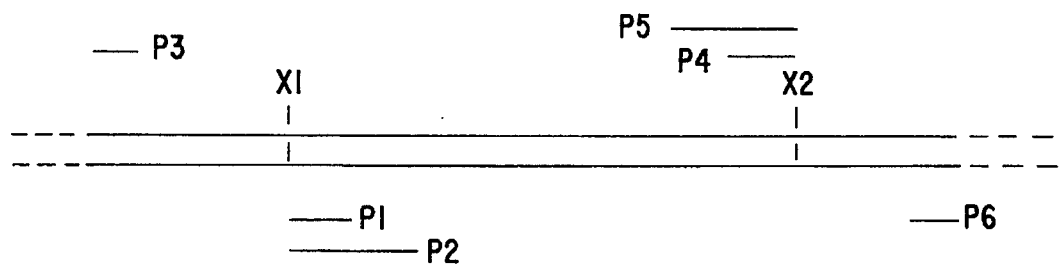
Figure 10:
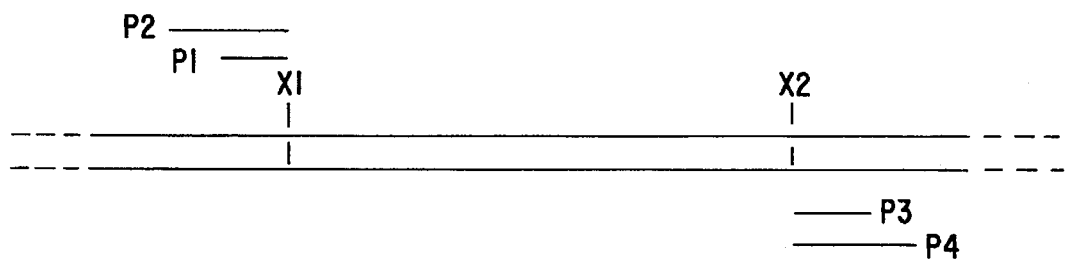

This step is a PCR with the primers P1, P2 and the compelemtary strand primer P7 (5' to complementary strand primer P3 from FIG. 2, SEQ ID NO 5).

The additional complementary strand primer was used to eliminate primer dimer problems. With a high number of cycles, both primer P7 and primer P3 produce primer dimers. Under certain circumstances, the desired PCR product was no longer generated. Amplification with primer P7 (this 2nd reaction step) followed by another amplification with primer P3 (3rd reaction step) suppresses the formation of primerdimers.

In this reaction, the concentration of the normal-selective primer is significantly lower than the one of the mutant-selective primer. This is due to the fact that only the quantity of normal-selective primer that was present in the first reaction was used in the second reaction. Thus, a preferred amplification of the mutant allele is possible. The available quantity of normal-selective primer is, however, sufficient provided the reagent mixture does not contain a mutant allele in order to obtain a visible amplification product after the 3rd reaction step thus also allowing an internal control of the PCR reaction during pool screening.

Reagent mixture:
12 µl=reagent mixture of 1st reaction step
58 µl aliquot of reagent mixture
 1.4 µl primer P7 (51.1 ng/µl stock solution) SEQ ID NO 5
 0.7 µl Asa short (95.7 ng/µl stock solution) SEQ ID NO 1
 0.85 µl $Mg^{2+}$ from 20 mM $MgCl_2$ solution
 5.8 µl 10×PCR buffer without $Mg^{2+}$
 0.12 µl Taq-polymerase
 49.13 µl $H_2O$
70 µl total volume The samples were covered with appr. 50 µl heavy white mineral oil (Sigma Cat. No. 400-5)

Temperature intervals: 20×(1 min 95° C., 1 min 60° C., 1 min 72° C.)
4×(2 min 60° C., 2 min 72° C., 5 min 72° C.)

The purpose of the last four cycles (only annealing and extension, no denaturing) is to ensure that no more single-stranded DNA is present prior to preparing the mixture for the third reaction step.

3rd reaction step
PCR with complemetary strand primer P3

7 µl of the product from the 2nd reaction step
43 µl aliquot of reagent mixture
 0.5 µl primer 3 (92.4 ng/µl) SEQ ID NO 4
 0.65 µl Asa short, SEQ ID NO 1
 0.2 µl Asa long, SEQ ID NO 2
 5 µl 10×buffer without $Mg^{2+}$
 2.14 µl $Mg^{2+}$ from 10 mM $mgCl_2$ solution
 2.5 µl mixture of dNTP containing the four dNTPs of 100 µM each
 31.76 µl $H_2O$
 0.25 µl Taq polymerase (5 U/µl Beckmann)
50 µl total volume Temperature intervals: 40×(1 min 95° C., 1 min 65° C., 1 min 72° C.)
4×(2 min 65° C., 2 min 72° C., 5 min 72° C.)

In the second reaction, selectivity is essentially determined by the low dNTP concentration (2 µM) whereas the 60° C. annealing temperature is relatively low to ensure efficient annealing. As compared thereto, a much greater amount of dNTP is used in the third reaction so that the amount of product to be formed is correspondingly higher. Since the additional mutations in the primers were incorporated in the PCR products during the second reaction, the annealing temperature of the third reaction could be increased to 65° C.

When used for screening for the B3500 mutation, the pattern for pooling the samples was adjusted to the frequency of mutation among the population. The B3500 mutation occurs in 1 out of every 500 to 700 persons. The probes should be analyzed in three stages:

1. analysis of relatively large pools
2. analysis of smaller pools formed from the larger pools
3. analysis of individual probes 8 samples of EDTA blood were mixed to form primary pools and one aliquot was obtained from each of these pools to produce a 64-sample pool. This is an optimum pattern for a three-step analysis at a mutation frequency of 1 in $8^3$, i.e. 1 in 512. The pattern can also be applied over a wide range of other frequency rates.

When mixing the EDTA samples, the various leukocyte concentrations of the individual samples were accounted for by different volumes. The number of leukocytes used in the pools was hence the same for each test subject. First, for each test subject 100 µl EDTA-blood were pipetted onto a microliter plate so that the subsequent pipetting could be performed by a pipetting roboter (Tecan RSP 5052, Zinsser Analytic, Frankfurt). The instrument first diluted each sample with 100 µl of 0.9% NaCl solution and combined aliquots of appr. 8000 eukocytes to form the primary 8-sample pools (volumes calculated from leukocyte concentrations by the computer). From each of the 8-sample pools (after mixing by the instrument), 160000 leukocytes were pipened into 64-sample pools. DNA isolation was first carried out for the 64-sample pools only. Appr. 4100 sample were analyzed in this manner. Six 64-sample pools which contained the mutant sequence were found in this procedure. The DNA of the corresponding 8-sample pools was isolated and analyzed in the same way as the 64-sample pool. Then, the DNA of the individual samples that were identified as positive in the 8-sample pool was isolated and assayed according to example 1. 6 heterozygous carrier were thus identified.

Only a normal band was obtained for the negative control. When the oligonucleotide mixture is prepared slightly differently (less ASA), it is possible that the band at the position of the mutant product is always somewhat weaker for negative controls. This is the highest level of sensitivity possible with this systems since mispriming and errors of the Taq polymerase during the synthesis of the complementary strand now produce a background that is barely visible. This ensures that even small amounts of actually present mutant originals are detected (the normal band then disappears) provided they excced the background.

Figure 12:
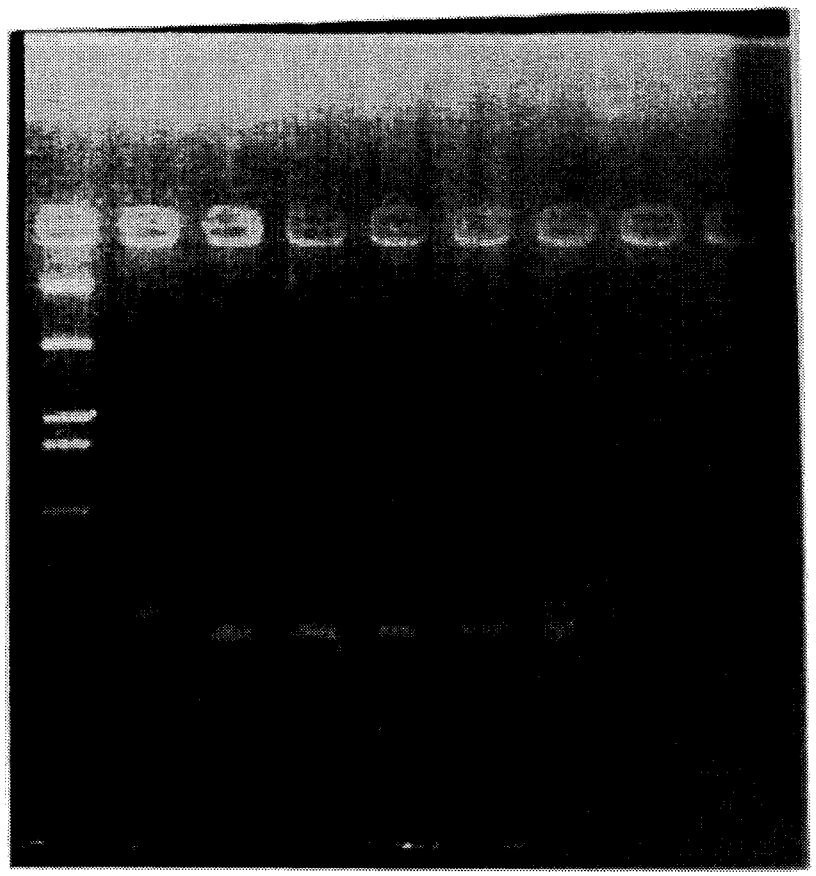
FIG. 12 shows the analysis of the probes amplified in example 2 and a negative control.
Figure 13:
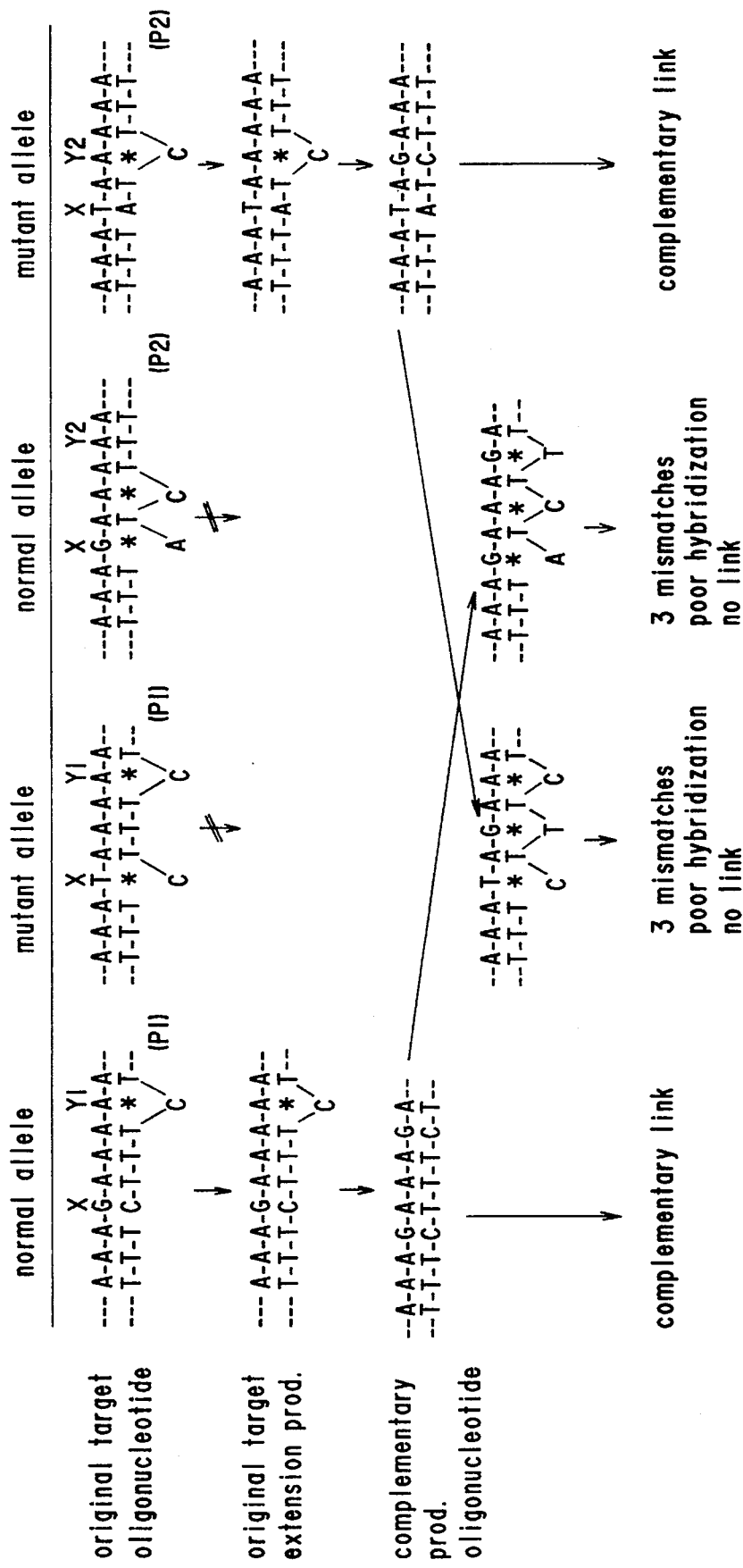
FIG. 13 shows use of an LCR in the method of the invention.

FIG. 12 shows the analysis of amplified probes and of one negative control. Whereas only the long PCR product occurs during negative control (134 bp, lane 2), 3 and 4 show only the mutant PCR product (114 bp). In the dilutions of 5 to 7, the mutant PCR product prevails and a very small portion of normal product is also found. With the method described it is hence possible to detect the DNA of a heterozygote test subject even in a mixture that contains the DNA of 800 normal test subjects. Higher dilutions have not yet been tested.

1: standard of length
2: negative control
3: 1:50
4: 1:100
5. 1:200
5: 1:400
6. 1:800

EXAMPLE 3

Method using for one of the alleles an oligonucleotide which cannot be extended

Expecially in multiplex processes, oligonucleotide extension can be blocked, for example, by incorporating a dideoxynucleotide at the 3'-end (Cozzarelli et al. (1969) *Journal of Molecular Biology 45:513*). In a multiplex process which serves to determine the presence of one (or more) of several known (rare) mutations, the normal alleles are thus excluded from amplification so that the number of amplification products for each test subject is normally limited to 1–3 bands (1 normal band is included in the amplification for control, 1–2 bands of mutant primary annealing step may occur when blocked oligonucleotides which are perfectly complementary to the original target are subseqently added.

If variant 2 is used to estimate the approximate concentration of an allele or an isolate of an infectious agent or a somatic mutant (oncogene), it is possible to use a third artifical allele as a standard. A primer in accordance with invention with a 3'-OH end is used for this latter allele and the allele to be estimated whereas the amplification of all other alleles is obstructed by dideoxyoligonucleotides. The artifical third allele can already contain the Y-differences of the corresponding primer. Depending on the extent to which the primer directly matches the template, it has a relatively large number of Y positions to ensure separate amplifcations.

When nucleotides polymerize into polynucleotides, a phosphodiesterbond links the 5'-OH group to the 3'-OH group. A dideoxynucleotide has no 3'-OH group. The end of a nucleic acid can hence not be extended with dideoxynucleotides. This effect is used in sequencing procedures, for example. In a multiplex procedure, however, numerous bands are formed which are rather confusing at first. Our laboratory, for example, already used variant 2 (allele-specific primer) to perform a multiplexing procedure for five mutations in one reagent mixture. At least 5 bands (normal persons or mutations) occur in this process. If a person is heterozygous for two mutations the number of bands even increases to seven. If, however, the testing of a certain gene (in this case LCAT, but also LDL receptor, for example) and certain person is limited to establishing the absence or presence of a known mutation, it is not necessary to amplify the normal alleles (except for one band as a PCR control). In a normal person, the number of bands is then reduced to one. Only one band will be added per mutation. The total yield of the PCR is distributed over significantly less bands and the band pattern is simplified. If, for example, one out of 40 different possible defects was detected (in several multiplex reactions), it is then possible to test for for heterozygosity or homozygosity (using a normal -primer instead of a dideoxy primer). A dideoxyoligonucleotide (for each mutation site) may serve to cover the allele in such a multiplexing procedure thus excluding hybridization with an incorrect COP primer, for example. Because of the remaing primers of the invention the mutant primer perfectly matches a possibly occurring PCR product of the mutant allele. In variant 2 (allele-specific primer, incorrect annealing and priming of the other primer could be reduced by using a dideoxyoligonucleotide.

Analogously, it is possible to use 5'-end oligonucleotides in LCR reactions. In promotor-controlled variants, one of the above oligonucleotides or a primer containing a non-active variant of the promotor sequence can be used analogously.

Sequence Protocol

SEQ ID NO 1

| | |
|---|---|
| Sequence length: | 29 bases |
| Type of sequence: | deoxyribonucleotide sequence |
| Type of strand: | single strand |
| Topology: | linear |
| Position: | 10658–10686 (J. Biol. Chem. (1986) 261: 12918–12921) |

3'-TGAGAAGTCA CTTCGACGTC CCGTGAAGG-5'

SEQ ID NO 2

| | |
|---|---|
| Sequence length: | 49 bases |
| Type of sequence: | deoxyribonucleotide sequence |
| Type of strand: | single strand |
| Topology: | linear |
| Position: | 10658–10706 |

3'-CCATAAGTCA CTTCGACGTC CCGTGAACCT TTTAACTACT ATAGACCTT-5'

SEQ ID NO 3

| | |
|---|---|
| Sequence length: | 49 bases |
| Type of sequence: | deoxyribonucleotide sequence |
| Type of strand: | single strand |
| Topology: | linear |
| Position: | 10658–10706 |

3'-CGAGAAGTCA CTTCGACGTC CCGTGAACCT TTTAACTACT ATAGACCTT-5'

SEQ ID NO 4

| | |
|---|---|
| Sequence length: | 28 bases |
| Type of sequence: | deoxyribonucleotide sequence |
| Type of strand: | single strand |
| Topology: | linear |
| Position: | 10573–10600 |

5'-GATGTCAAGG GTTCGGTTCT TTCTCGGG-3'

SEQ ID NO 5

| | |
|---|---|
| Sequence length: | 31 bases |
| Type of sequence: | deoxyribonucleotide sequence |
| Type of strand: | single strand |

-continued

Sequence Protocol

Topology: linear
Position: 10532–10562
5'-GCCTCACCTC TTACTTTTCC ATTGAGTCAT C-3'
One of ordinary skill in the art would be able to make the oligonucleotides of the present invention by following the disclosure of U.S. Pat. No. 4,415,732, which is hereby incorporated by reference for the teachings of such oligonucleotides production therein.

We claim:

1. A method of detecting variant nucleic acids whose nucleotide sequences differ from one another in at least one position X, comprising the steps of:
   a) in a single reaction vessel combining a set of oligonucleotides, whose nucleotide sequences differ from one another in a position which corresponds to position X and in at least one additional position Y, with the nucleic acids to be detected under hybridization conditions,
   b) extending any oligonucleotides which hybridize to the nucleic acids to be detected to form extension products, wherein said nucleic acids are used as templates,
   c) denaturing the complexes of said variant nucleic acids and said extension products,
   d) hybridizing said extension products with an oligonucleotide, wherein at least a portion of the oligonucleotide is fully complementary to a portion of said extension products,
   e) extending any oligonucleotides which hybridize to said extension products formed in step b) to form nucleic acids complementary to at least a part of said extension products,
   f) combining oligonucleotides of said set of oligonucleotides of step a) with the complementary nucleic acids formed in step e),
   g) extending any oligonucleotides which hybridize to the complementary nucleic acids formed in step e) to form nucleic acids, and
   h) detecting the nucleic acids formed in step e) or step g).

2. The method according to claim 1, wherein a nucleotide, which corresponds to position X on the oligonucleotide, is complementary to position X of one nucleic acid sequence to be detected but not to position X of the other nucleic acid sequences.

3. The method according to claim 1, wherein the oligonucleotides terminate with a nucleotide which corresponds to position X.

4. The method according to claim 1, wherein the Y position is located 1 to 8 nucleotides away from a terminal nucleotide.

5. The method according to claim 1, wherein the Y position is located 1 to 3 nucleotides away from a terminal nucleotide.

6. The method according to claim 1, wherein positions X and Y are 1 to 8 nucleotides apart.

7. The method according to claim 1, wherein positions X and Y are 1 to 3 nucleotides apart.

8. The method according to claim 1, wherein positions X and Y are located on a part of an oligonucleotide of the set of oligonucleotides which hybridizes to a nucleic acid to be detected.

9. The method according to claim 1, wherein the oligonucleotides differ in length.

10. The method according to claim 1, wherein the oligonucleotides have different detectable labels.

11. The method according to claim 1, wherein the nucleic acids formed in step e) or step g) are bound to a solid phase before said detecting step h).

12. The method according to claim 1, wherein said variant nucleic acids to be detected are alleles.

13. The method according to claim 1, wherein said variant nucleic acids to be detected belong to different species of infectious agents.

14. The method according to claim 1, wherein said variant nucleic acids to be detected belong to different species, sub-species or strains of infectious agents.

15. The method according to claim 1, further comprising the addition, before step a) of one variant nucleic acid as a detectable control nucleic acid.

16. The method according to claim 1, wherein said variant nucleic acids contain mutations relative to a given nucleic acid.

17. The method according to claim 1, wherein said detecting step h) comprises:
   i) denaturing the nucleic acids formed in step e) or step g),
   ii) adding under hybridization conditions a second set of oligonucleotides to detect the extension products formed in step e), wherein each member of said second set of oligonucleotides comprises:
      α) a sequence identical to a part of the sequence of an oligonucleotide from the set of oligonucleotides according to claim 1, and
      β) a sequence identical to a part of a sequence which was added to said oligonucleotide from the set of oligonucleotides according to claim 1 in said extending step b), and
   iii) detecting hybridization products formed in step ii).

18. The method according to claim 1, wherein the detecting step h) comprises:
   i) denaturing the nucleic acids formed in step e) or step g),
   ii) adding under hybridization conditions a second set of oligonucleotides to detect the extension products formed in step g), wherein each member of said second set of oligonucleotides comprises:
      α) a sequence complementary to a part of the sequence of an oligonucleotide from the set of oligonucleotides according to claim 1, and
      β) a sequence complementary to a part of a sequence which was added to said oligonucleotide from the set of oligonucleotides according to claim 1 in said extending step b), and
   iii) detecting the hybridization products formed in step ii).

19. The method according to claim 17, wherein at least one oligonucleotide of said second set of oligonucleotides contains at least one immobilizable or one detectable label.

20. The method according to claim 18, wherein at least one oligonucleotide of said second set of oligonucleotides contains at least one immobilizable or one detectable label.

21. The method according to claim 1, wherein one of the oligonucleotides of said set of oligonucleotides differs from the sequence of another oligonucleotide in said set of oligonucleotides in that said one oligonucleotide has an additional number of nucleotides at one end and the other end of the same oligonucleotide lacks the same number of nucleotides as said additional number of nucleotides at said one end.

22. A method of detecting variant nucleic acids whose nucleotide sequences differ from one another in at least one position X, comprising the steps of:
   a) in a single reaction vessel combining a set of oligonucleotides, whose nucleotide sequences differ from one another in a position which corresponds to position X and in at least one additional position Y, with the nucleic acids to be detected under hybridization conditions,
   b) extending any oligonucleotides which hybridize to the nucleic acids to be detected by linking nucleotides, oligonucleotides, or nucleotide analogues to form extension products, wherein said nucleic acids are used as templates,
   c) denaturing the complexes of said variant nucleic acids and said extension products,
   d) hybridizing said extension products with an oligonucleotide, wherein at least a portion of the oligonucleotide is fully complementary to a portion of said extension products,
   e) extending any oligonucleotides which hybridize to said extension products formed in step b) to form nucleic acids complementary to at least a part of said extension products,
   f) combining oligonucleotides of said set of oligonucleotides of step a) with the complementary nucleic acids formed in step e),
   g) extending any oligonucleotides which hybridize to the complementary nucleic acids formed in step e) to form nucleic acids, and
   h) detecting the nucleic acids formed in step e) or step g).

* * * * *

SEQUENCE LISTING ( 1 ) GENERAL INFORMATION:

( i i i ) NUMBER OF SEQUENCES: 5

( 2 ) INFORMATION FOR SEQ ID NO:1:

( i ) SEQUENCE CHARACTERISTICS:
( A ) LENGTH: 29 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:1:

GGAAGTGCCC TGCAGCTTCA CTGAAGAGT 29

( 2 ) INFORMATION FOR SEQ ID NO:2:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:2:

TTCCAGATAT CATCAATTTT CCAAGTGCCC TGCAGCTTCA CTGAATACC 49

( 2 ) INFORMATION FOR SEQ ID NO:3:

( i ) SEQUENCE CHARACTERISTICS:
( A ) LENGTH: 49 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:3:

TTCCAGATAT CATCAATTTT CCAAGTGCCC TGCAGCTTCA CTGAAGAGC 49

( 2 ) INFORMATION FOR SEQ ID NO:4:

( i ) SEQUENCE CHARACTERISTICS:
( A ) LENGTH: 28 base pairs
( B ) TYPE: nucleic acid
( C ) STRANDEDNESS: single
( D ) TOPOLOGY: linear ( i i ) MOLECULE TYPE: DNA ( x i ) SEQUENCE DESCRIPTION: SEQ ID NO:4:

GATGTCAAGG GTTCGGTTCT TTCTCGGG 28

( 2 ) INFORMATION FOR SEQ ID NO:5:

( i ) SEQUENCE CHARACTERISTICS:
      ( A ) LENGTH: 31 base pairs
      ( B ) TYPE: nucleic acid
      ( C ) STRANDEDNESS: single
      ( D ) TOPOLOGY: linear ( i i ) MOLECULE TYPE: DNA ( x i ) SEQUENCE DESCRIPTION: SEQ ID NO:5:

GCCTCACCTC TTACTTTTCC ATTGAGTCAT C    31